United States Patent [19]

Arditty et al.

[11] Patent Number: 4,907,878
[45] Date of Patent: Mar. 13, 1990

[54] DEVICE FOR DISCRIMINATING FLUIDS HAVING DIFFERENT REFRACTIVE INDICES AND DEVICE FOR MEASURING THE VOLUMINAL FRACTION OF AT LEAST ONE FLUID OF A CURRENT OF NON-MIXIBLE FLUIDS INCORPORATING THE DISCRIMINATION DEVICE

[75] Inventors: Hervé Arditty, Marly Le Roi; Gilles Le Boudec, Saint Germain en Laye; Philippe Graindorge, Magny les Hameaux; Jean-Pierre Gerardin, Nanterre; Jean-Louis Lesne, Meudon; Dominique Meyet, Paris, all of France

[73] Assignee: Electricite De France, Paris, France

[21] Appl. No.: 934,980

[22] Filed: Nov. 25, 1986

[30] Foreign Application Priority Data

Nov. 27, 1985 [FR] France .................. 85 17527

[51] Int. Cl.⁴ .................................. G01N 21/43
[52] U.S. Cl. ......................... 356/128; 356/133
[58] Field of Search ............. 356/133, 128, 136; 350/96.17

[56] References Cited

U.S. PATENT DOCUMENTS 3,867,033  2/1975  Hasinger .
3,969,014  7/1976  Auracher .................. 350/96.17
4,544,840 10/1985  Keller ......................... 356/133

FOREIGN PATENT DOCUMENTS 1927330  1/1970  Fed. Rep. of Germany .
3302089  7/1984  Fed. Rep. of Germany .
2130037 11/1972  France .

OTHER PUBLICATIONS

Patents Abstracts of Japan, vol. 3, No. 113 (E-139), 19 Sep. 1979, p. 3, E-139; & JP-A-5489680 (Matsushita Denki Sangyo K.K.) 16-07-1979.
First International Conference on Optical Fibre Sensors, 26-28 Apr. 1983, pp. 96-99, IEE, Londres, GB; K. Spenner et al.: "Experimental Investigation of Fiber Optic Liquid Level Sensors and Refractommeters".
NachrichtenTechnik Elektronik, vol. 33, No. 11, 1983, pp. 444-448, Berlin-Est., DD; St. Lochmann et al.: "Passive Optische Verzweigungselemente", p. 446, paragraphe 3.1.2.
Applied Optics, vol. 21, No. 5, 1er Mars. 1982, pp. 886-892, New York, U.S., M. A. Vince et al.: "Optical Probe for High Temperature Local Void Fraction Determination", pp. 886-887, 892.
"An Optical Probe for Detecting Liquid Interfaces", Geake Journal of Physics E: Scientific Instruments, 1975, vol. 8, pp. 860-863.

Primary Examiner—Richard A. Rosenberger
Attorney, Agent, or Firm—Sughrue, Mion, Zinn, Macpeak & Seas

[57] ABSTRACT

The discriminating device comprises an optical coupler (4) having at least three ends (5 to 8) to which are connected a semiconductor source of light (1) whose intensity is modulated, a semiconductor photoconductor (2) and an optical probe constituted by a multi-mode optical fibre (3) whose end has a pointed shape. This discriminating device is in particular applicable in a device for measuring the voluminal fraction of at least one fluid of a current of non-mixible fluids.

13 Claims, 3 Drawing Sheets

DEVICE FOR DISCRIMINATING FLUIDS HAVING DIFFERENT REFRACTIVE INDICES AND DEVICE FOR MEASURING THE VOLUMINAL FRACTION OF AT LEAST ONE FLUID OF A CURRENT OF NON-MIXIBLE FLUIDS INCORPORATING THE DISCRIMINATION DEVICE

BACKGROUND OF THE INVENTION

The present invention relates to a device for discriminating fluids of different refractive indices and to a device for measuring the voluminal fraction of at least one fluid of a current of non-mixable fluids comprising the application of the discriminating device. The term "current" used in this description means a relative movement of the fluids of the current relative to the detector of a discriminating or measuring device.

The principle of operation of such a fluid discriminating device is based on the difference between the indices of refraction, for example between a gas or a vacuum (equal to 1) and a liquid (in respect of water 1.3). Indeed, when a beam of light propagated in a multimode optical fibre reaches its end, the coefficient of reflection undergone by the beam depends on the difference between the refraction indices between the fibre and the outer medium in contact with the end of the fibre. Thus, by measuring the returning light, it is possible to deduce therefrom at any moment the index of refraction of the fluid in contact with the end of the fibre, and therefore the nature of the fluid (gas or liquid). By effecting a mean with respect to time, there is obtained the local voluminal fraction of each fluid in the current in the region of the end of the probe and it is then possible to obtain the voluminal fraction by extension to a certain volume around the end of the fibre as a function of the chosen hydraulic model.

Known devices performing such a function comprise a gas laser for example of the helium-neon type, whose beam is coupled in a multimode optical fibre by optical coupling means (lens) after having passed through a separating strip, this fibre being used directly as a measuring probe. The reflected beam is received by a photomultiplier. The use of a photomultiplier rendered necessary by optical losses of the chain, and its association with a gas laser and optical coupling elements, require mechanical assemblies and result in a large and relatively fragile device. Moreover, owing to the arrangement using a single fibre, the measuring probe, subjected to severe surrounding stresses, can only be replaced by completely disassembling the device. Lastly, as the laser is a continuous laser, the return light cannot be distinguished from the surrounding light without the use of an additional costly, fragile, large or limiting device and it is therefore necessary to maintain this surrounding light at a sufficiently low level.

SUMMARY OF THE INVENTION

An object of the invention is to provide a discriminating device which reduces the optical losses and has a reduced overall size and fragility and a high signal-to-noise ratio and a short rise time.

The invention therefore provides a device for discriminating fluids of different refractive indices which comprises an optical fibre coupler having at least three ends to which there are connected a semiconductor light source whose intensity is modulated, a semiconductor photodetector and an optical probe constituted by a multimode optical fibre having the same index profile as the fibres of the coupler whose end has a pointed shape obtained by a hot drawing out thereof.

Advantageously, the circuit for modulating the source of light is connected to a synchronous amplifier for de-modulating and filtering the output signal of the photodetector, and the discriminating device further comprises a circuit for discriminating levels at one or more predetermined thresholds receiving the output signal of the synchronous amplifier.

Such a discriminating device is advantageously applicable in a device for measuring the voluminal fraction of at least one fluid of a current of non-mixable fluids comprising such a discriminating device and a circuit for integrating the output signal of the level discriminating circuit.

A better understanding of the invention will be had from the following description which is given merely by way of example with reference to the accompanying drawings, in which:

DETAILED DESCRIPTION OF THE PREFERRED EMBODIMENTS

Figure 1:
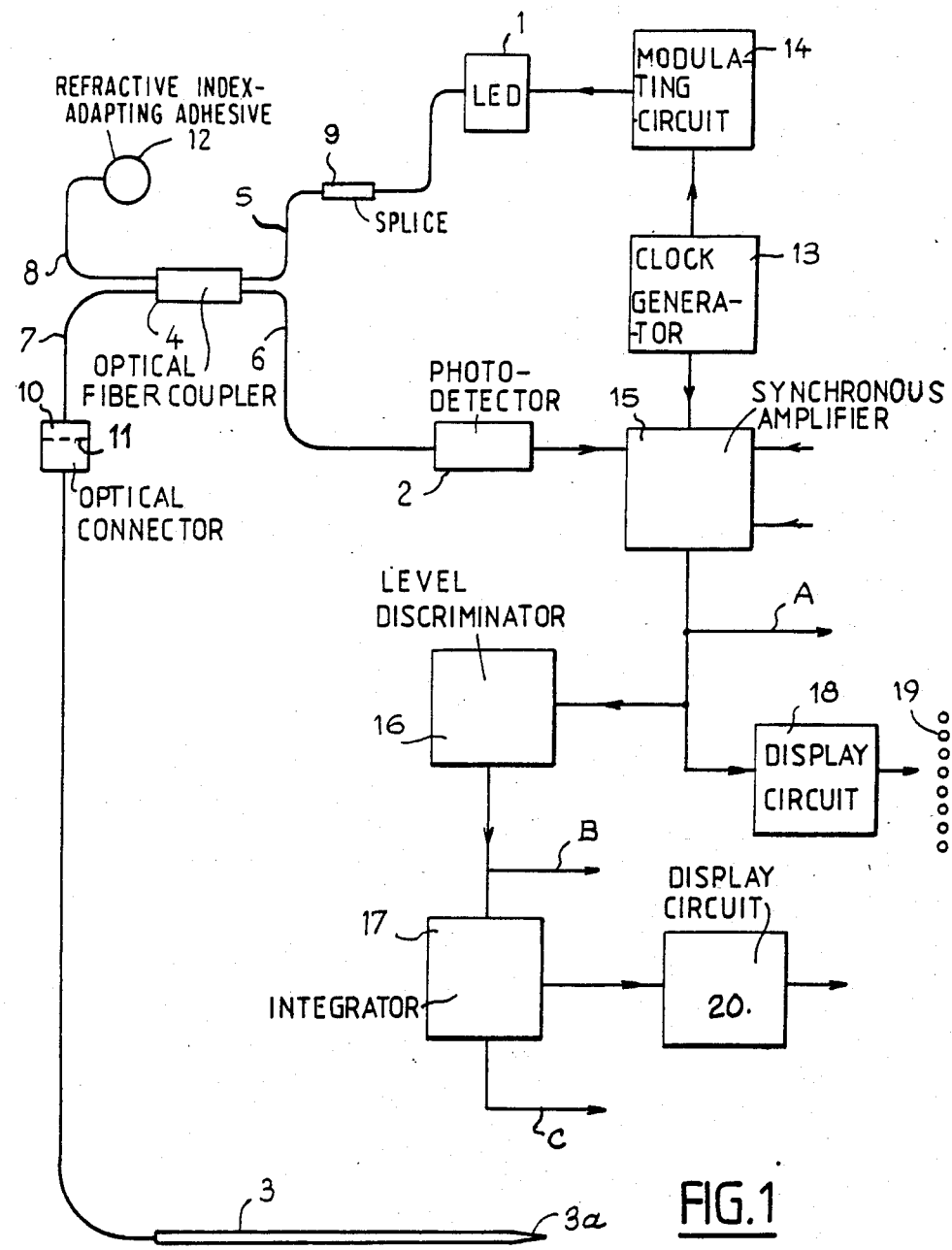
FIG. 1 is a block diagram of a measuring device comprising a discriminating device according to the invention.

The measuring device of FIG. 1 comprises a light-emitting diode 1 provided with a starting fibre constituting the source of light (this source of light may possibly be replaced by a semiconductor laser, a photodetector 2 and a detecting optical fibre 3 or measuring probe, these elements being interconnected by an optical fibre coupler 4. The characteristics of the optical fibre, which is preferably a fibre having a refractive index gradient, are related to those of the diode 1. All of the fibres of the device have an identical refractive index profile.

Figure 2:
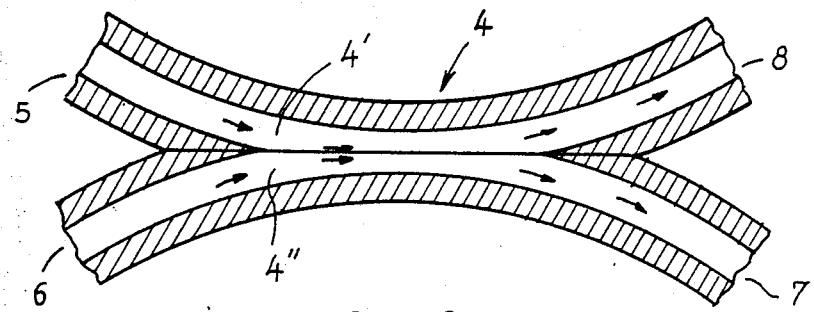
FIG. 2 is a diagram of an optical coupler used in the device of FIG. 1.

This coupler comprises four fibre ends 5 to 8 and its structure is diagrammatically represented in FIG. 2. This coupler consists of two optical fibres whose cores 4' and 4" are put into optical interaction by a thermal fusion or by a polishing and the putting into contact of the parts of the two fibres which must interact. The four ends of the fibres perform symmetrical functions in pairs: the light transmitted to the end of the fibre 5 is thus equally divided between the two ends of the fibres 7 and 8 by the fibre portions which interact. The end 6 performs the same function as the end 5 and, in the same way, the side 7, 8 is symmetrical with the side 5, 6 if the direction of propagation is reversed.

By way of example, all the fibres of the device may be fibres of the type 100–140 having a refractive index gradient and the light-emitting diode may be chosen with a power of 100 microwatts at the end of the starting fibre.

As can be seen in FIG. 1, the end 5 of the coupler 4 is connected to the diode 1 through a splice 9, and the end 6 is connected to the photodetector 2. The photodetector may also be merely mechanically positioned in confronting relation to the fibre end 6.

The detecting optical fibre is connected to the end 7 of the coupler through an optical connector 10, for example of the type SMA 906 or 905 sold by the firm Amphenol, which permits the simple and rapid disconnection of the measuring probe, an easy replacement of the latter and the possible addition of an extension. This connection is adapted in respect of the index of refraction, i.e. between the two connector parts there is a liquid film 11 whose refractive index is equal to the mean refractive index of the core of the fibres. Thus, no parasitic reflection is produced by the connector. Likewise, the last fibre end 8 of the coupler 4 is coated with an index-adapting adhesive 12 (i.e. its index of refraction is equal to that of the fibre). Thus, the light propagated in this fibre end does not undergo reflection at its end and therefore does not create a parasitic signal. It will be understood that this fibre end may be connected to another optical detecting probe by providing an optical connector between this adhesive-coated end and the optical coupler. There may also be envisaged an optical coupler comprising more than two fibres whose cores are put into optical interaction.

Figure 3:
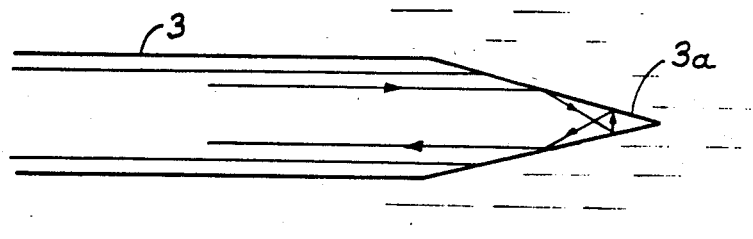
FIG. 3 is a diagram of the optical fibre used in the device of FIG. 1.

The manner in which the end of the detecting fibre 3 is treated plays a very important part in the operation of the device. Indeed, if the probe is simply the split end of an optical fibre, hydrodynamic effects will disturb the operation of the device. When the planar surface of the fibre enters the liquid medium or gaseous medium, a progressive drying effect is produced with the result that the reflection signal slowly increases at the rate at which the liquid dries. This effect is related to phenomena of capillarity on the surface of the end 3a of the fibre 3. It is eliminated if the end of the fibre 1 is rendered rather fine by drawing out the fibre end 3a to a point. This drawing out is achieved by heating the fibre to its softening point (FIG. 3) and exerting a traction on the fibre. The result is an end portion of conical shape whose apex angle is very small (less than 10°). This manufacturing method enables the core-cladding structure of the fibre to be maintained right to the end of the cone. Moreover, this end has an extremely small radius of curvature (less than 20 microns). The properties of a fibre end produced by this method are the following:

complete absence of a drying effect; indeed, the radius of curvature of the end is small enough to ensure that the forces of capillarity are insufficient to maintain a drop of liquid on the point of the fibre; the longer response time of the detector related to the capillarity effects is thus completely avoided;

a coefficient of reflection very close to one, when the end is in a gaseous medium; indeed, the fact that the structure of the fibre is conserved in the conical region and the hot and controlled shaping of the end portion result in a total internal reflection effect of the whole of the beam at the end of the fibre when the latter is located in a gaseous medium; this considerably improves the quality of the return signal and facilitates the processing;

a very short liquid-gas and gas-liquid transition time owing to the small size of the interaction zone.

Further, this production method is relatively easy to carry out and results in very good manufacturing yields and a good reproducibility of the performances.

The light-emitting diode 1 is compatible with low voltage electronic technology for its current supply and its modulation, the advantages of which will be explained hereinafter. Thus, the measuring device according to the invention comprises a clock signal generator 13 of which a first output is connected to a modulating circuit 14. The output of the circuit 14 is connected to the input of the light-emitting diode and thus permits the modulation of the light emitted. The modulation frequency is so chosen as to be about ten times higher than the desired rise time of the output signal of the photodetector, for example one MHz for a rise time of ten microseconds. The diode 1 transmits modulated light through the coupler 4 to the optical fibre 3 and the light reflected at the end of the fibre, related to the refraction index of the medium in contact with the point of the fibre 1, is detected by the photodetector 2 after having passed through the coupler 4. The output of the photodetector 2 is connected to a synchronous amplifier 15 for demodulating the detected light in return or useful signal. This modulation is effected by multiplication of the return signal by the output signal of the clock circuit 13 and by filtering of the resulting signal by means of a low-pass filter included in the amplifier 15. In this way, there is obtained a complete insensitivity in the surrounding light and a high signal-to-noise ratio.

Figure 4A:
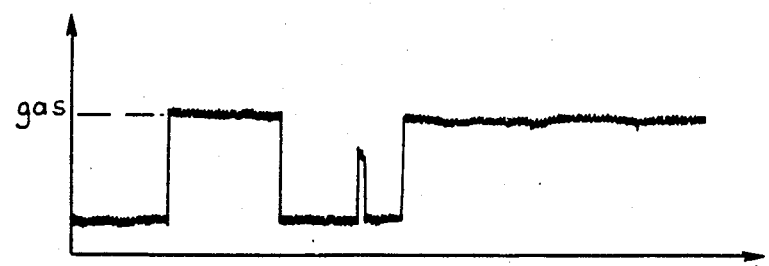
FIGS. 4A to 4C represent signals taken at various points of the device of FIG. 1.
Figure 4B:
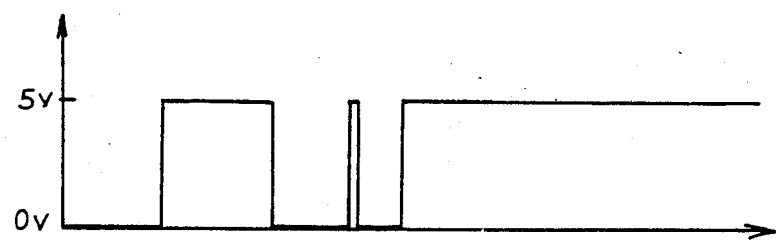

The analog signal delivered by the photodetector therefore essentially contains two electric levels: the level corresponding to the liquid phase and that of the gaseous phase. This analog signal at the output A of the amplifier 15 is represented in FIG. 4A. A circuit 16 for discriminating levels having one threshold permits the obtainment at its output B a logic signal having two states represented in FIG. 4B. The voltages of these two states are then perfectly known. It is of course possible, by means of a discriminating circuit having a plurality of thresholds, to discriminate more than two fluids of different indices. The signal at point B may be advantageously used for measuring the grain size of the current. Indeed, by measuring the periods during which the signal is in the high state (or in the low state or at a given level), it is possible to deduce the diameter of the bubbles of gas or vacuum of the current by dividing these measurements by the flow velocity of the current. By then drawing up a graph of the distribution as a function of the number of bubbles of each diameter for a series of predetermined diameters, a measurement of the grain size of the current is obtained.

Figure 4C:
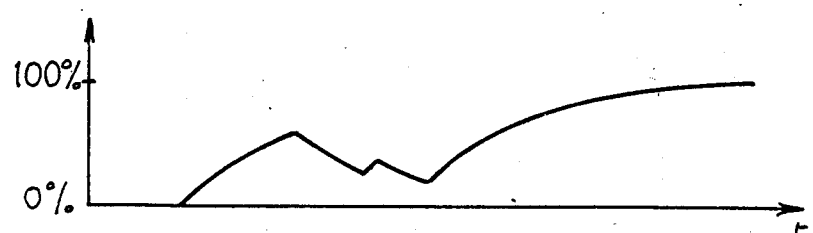

An advantageous application of such a discriminating device resides in the measurement of the voluminal fraction of at least one fluid of a current of non-mixible fluids, i.e. there exists a relative movement of the current relative to the detecting optical fibre. For this purpose, an integration is effected of the signal at two output states of the circuit 16 by means of an integrator circuit 17 so as to obtain at its output C a value of the local voluminal fraction of gas in the current (FIG. 4C) which is extremely precise, owing to the absence of noise in the logic signal and the precision with which the voltages of the two logic states can be controlled. This logic signal may also be used for operations for counting or measuring durations of two phases.

A number of secondary functions may be added to the basic measuring device so as to render its utilization more easy:

the read-out of the analog signal level by a luminous scale by means of a display circuit 18 and a series of light-emitting diodes 19; in this way, the two analog levels corresponding to the liquid and the gas can be seen at a glance;

the numerical display of the voluminal fraction of gas obtained by the filtering of the logic signal by means of a display circuit 20 and a three digit read-out, for example;

the regulation of the offset and the gain of the amplifier for respectively compensating for a parasitic reflection due to a defective connector and the optical loss in a connector or a very long fibre; the effect of the adjustment is displayed by the light scale so that this adjustment is rapid and simple to carry out.

The device for discriminating fluids of different refractive indices such as described hereinbefore has many advantages over prior measuring devices. These advantages are, among others, a configuration employing cheap components of reduced overall size (the whole of the optical part of the device may for example occupy a volume between 10 and 20 cm$^3$), a high gain of reflectivity of the probe and a very short optical rise time owing to the drawn out end portion of the detection fibre, an easy removal of the detection fibre, for example for its replacement, owing to the optical connector 10, a very good signal-to-noise ratio owing to the synchronous modulation, and possibilities of establishing numerous items of information which facilitate its utilization in a device for measuring the voluminal fraction of at least one fluid of a current of non-mixible fluids.

These discriminating and measuring devices have many applications in aerosols (grain size of the droplets in suspension in a gas for example for the mists or mixtures for internal combustion engine carburettors), for the measurement and the control of the efficiency of a low temperature thermodynamic cycle (water-steam mixture) or in mixtures of non-mixible liquids in the chemical, agroalimentation and petrochemical industries (water-petroleum current).

What is claimed is:

1. A device for discriminating fluids having different refractive indices, comprising in combination an optical fibre coupler with optical fibers having at least three ends, a semiconductor source of light combined with a circuit for modulating the intensity of said source of light and connected to one of said three ends, a semiconductor photodetector connected to another of said three ends, and an optical probe connected to a third of said three ends and comprising a multimode optical fibre which has the same refractive index profile as the fibres of the coupler and an end portion in the shape of a point; said end portion being constituted by a cone having a radius of curvature which is small enough to ensure that the forces of capillarity are insufficient to maintain a drop of liquid on said pointed end portion when said probe is in a liquid medium and to produce a total internal reflection effect of said light at said pointed end portion when the probe is in gaseous medium.

2. A device for discriminating fluids having different refractive indices, comprising in combination an optical fibre coupler with optical fibers having at least three ends, a semiconductor source of light combined with a circuit for modulating the intensity of said source of light and connected to one of said three ends, a semiconductor photodetector connected to another of said three ends, and an optical probe connected to a third of said three ends and comprising a multimode optical fibre which has the same refractive index profile as the fibres of the coupler and an end portion in the shape of a point obtained by a hot drawing out of said end portion; wherein, when it has been drawn out, said pointed end portion is constituted by a cone which has an apex angle of less than 10° and a core-cladding structure which is conserved right to the end of said pointed portion.

3. A device according to claim 2, wherein the end of said cone has a radius of curvature of less than 20 microns.

4. A device according to claim 3, wherein said radius of curvature is small enough to ensure that the forces of capillarity are insufficient to maintain a drop of liquid on said pointed end portion when said probe is in a liquid medium, and to produce a total internal reflection effect of said light at said pointed end portion when the probe is in a gaseous medium.

5. A device according to claim 1 or 2, wherein multimode said optical fibre of the probe is a fibre having a refractive index gradient.

6. A device according to claim 1 or 2, comprising an optical connector connecting the third end of the coupler to the multimode optical fibre.

7. A device according to claim 6, wherein the optical connector has two separable parts, and a liquid film having a refractive index equal to the mean refractive index of the core of the optical fibres is disposed between the two separable parts of the optical connector.

8. A device according to claim 1 or 2, wherein the frequency of modulation of the source of light is higher than about 500 KHz.

9. A device according to claim 1, wherein said cone of said pointed end portion has an apex angle of less than 10° and a core-cladding structure which is conserved right to the end of said pointed end portion.

10. A device according to claim 9, wherein the end of said cone has a radius of curvature of less than 20 microns.

11. A device according to any one of claims 1, 9 or 10, wherein said end portion in the shape of the point of the multimode optical fibre forming the optical probe is obtained by a hot drawing out of said end portion.

12. A device for measuring the voluminal fraction of at least one fluid of a current of non-mixible fluids comprising a fluid discriminating device delivering an output signal, a circuit for integrating the output signal of the discriminating circuit, said discriminating device being adapted to discriminate fluids having different refractive indices and comprising in combination an optical fibre coupler having at least three ends, a semiconductor source of light combined with a circuit for modulating the intensity of said course of light and connected to one of said three ends, a semiconductor photodetector connected to another of said three ends, and an optical probe connected to a third of said three ends and comprising a multimode optical fibre which has the same refractive index profile as the fibres of the coupler and an end portion in the shape of a point obtained by a hot drawing out of said end portion, a synchronous amplifier for demodulating and filtering the output signal of the photodetector connected to said circuit for modulating said source of light and a circuit for discriminating levels at least one predetermined threshold connected to the synchronous amplifier for receiving an output signal of the synchronous amplifier; said multimode optical fibre having an end portion in the shape of a point; said end portion being constituted by a cone having a radius of curvature which is small enough to ensure that the forces of capillarity are insufficient to maintain a drop of liquid on said pointed end portion when said probe is in a liquid medium and to produce a total internal reflection effect of said light at said pointed end portion when the probe is in gaseous medium.

13. A method of making a device for discriminating fluids having different refractive indices, said device comprising in combination an optical fibre coupler with optical fibers having at least three ends, a semiconductor source of light combined with a circuit for modulating the intensity of said source of light and connected to one of said three ends, a semiconductor photodetector connected to another of said three ends, and an optical probe connected to a third of said three ends and comprising a multimode optical fibre which has the same refractive index profile as the fibres of the coupler and an end portion in the shape of a point; said end portion being constituted by a cone having a radius of curvature which is small enough to ensure that the forces of capillarity are insufficient to maintain a drop of liquid on said pointed end portion when said probe is in a liquid medium and to produce a total internal reflection effect of said light at said pointed end portion when the probe is in gaseous medium; said method comprising the steps of: heating said multimode optical fibre to its softening point; and drawing out the softened fibre to obtain said end portion in the shape of a point.

* * * * *